(12) United States Patent
Elian (10) Patent No.: US 7,462,442 B2
(45) Date of Patent: *Dec. 9, 2008

(54) BIOCOMPATIBLE MICROCHIP AND A METHOD FOR PRODUCING THE SAME

(75) Inventor: Klaus Elian, Erlangen (DE)

(73) Assignee: Infineon Technologies AG, Munich (DE)

( * ) Notice: Subject to any disclaimer, the term of this patent is extended or adjusted under 35 U.S.C. 154(b) by 138 days.

This patent is subject to a terminal disclaimer.

(21) Appl. No.: 10/491,143

(22) PCT Filed: Aug. 29, 2002

(86) PCT No.: PCT/DE02/03167

§ 371 (c)(1),
(2), (4) Date: Oct. 19, 2004

(87) PCT Pub. No.: WO03/032086

PCT Pub. Date: Apr. 17, 2003

(65) Prior Publication Data

US 2005/0042547 A1    Feb. 24, 2005

(30) Foreign Application Priority Data

Sep. 28, 2001  (DE) ................ 101 47 954

(51) Int. Cl.
*G03C 5/56* (2006.01)
(52) U.S. Cl. ............... 430/311; 430/322; 430/326; 602/48; 602/50; 602/32
(58) Field of Classification Search ............... None
See application file for complete search history.

(56) References Cited

U.S. PATENT DOCUMENTS

| | | | |
|---|---|---|---|
| 5,137,799 A | | 8/1992 | Kaempf et al. |
| 5,234,793 A | * | 8/1993 | Sebald et al. ............... 430/323 |
| 5,561,030 A | | 10/1996 | Holdcroft et al. ............ 430/311 |
| 5,776,659 A | * | 7/1998 | Watanabe et al. ........... 430/296 |
| 5,837,423 A | * | 11/1998 | Okamoto .................... 430/296 |
| 6,013,229 A | | 1/2000 | Lewis et al. |
| 6,066,438 A | | 5/2000 | Nicolau et al. |
| 6,106,993 A | * | 8/2000 | Watanabe et al. ......... 430/270.1 |
| 6,686,131 B2 | * | 2/2004 | Elian ........................... 430/322 |
| 2002/0081726 A1 | * | 6/2002 | Russell et al. ................ 435/366 |

FOREIGN PATENT DOCUMENTS

| | | |
|---|---|---|
| DE | 101 33 256 | 1/2003 |
| EP | 0 442 674 | 8/1991 |

OTHER PUBLICATIONS

Cui X et al.: "Electrochemical deposition and characterization of conducting polymer polypyrrole/PSS on multichannel neural probes" Sensors and Actuators A, Elsevier Sequoia S.A., Lausanne, Ch, Bd. 93, Nr. 1, Aug 25, 2001, Seiten 8-18, XP004255500; ISSN: 0924-4247 das ganz Dokument.

Cui, Xinyan et al: "Surface Modification of Neural Recording Electrodes with Conducting Polymer/Biomolecule Blends" Journal of Biomedical Materials Research, Bd. 56, Nr. 2 Apr. 30, 2001 Seiten 261-272, XP008015603 Wiley, New York, NY, US ISSN: 0021-9304 das ganze Dokument; International Search Report.

* cited by examiner

*Primary Examiner*—Daborah Chacko Davis
(74) *Attorney, Agent, or Firm*—Slater & Matsil, L.L.P.

(57) ABSTRACT

The invention relates to a process for the production of biocompatible structures. For this purpose, a chemically amplified photoresist is applied to a substrate and is structured. The photoresist contains a first polymer which has anchor groups for linking a biocompatible compound and a second polymer which is electrically conductive. After the structuring of the resist, a solution of the biocompatible compound is applied so that the biocompatible compound is coordinated to the anchor groups of the polymer.

17 Claims, 3 Drawing Sheets

BIOCOMPATIBLE MICROCHIP AND A METHOD FOR PRODUCING THE SAME

BACKGROUND

1. Field

The invention relates to a process for producing biocompatible structures and to a biocompatible microchip.

2. Background Information

Bioelectronics is a rapidly developing research area that combines chemistry, biochemistry and physics. Its aim is to enable communication between electronic apparatuses and living cells. A primary feature of a bioelectronic component is an immobilization of a biomaterial on a conductive or semiconductive substrate and a conversion of biological functions associated with the biological material into electronic signals. Examples of microelectronic components by means of which biological functions can be influenced and controlled include cardiac pacemakers and inner ear auditory prostheses. The development of such bioelectronic components leads to increasingly complex systems, in which a large number of transmission channels for information transmission between an electronic component and the cells to be influenced are required. Thus, for example, retina implants or prostheses for walking/standing are being developed. For this purpose, it is necessary to develop implants which, with numerous contact points, can both stimulate nerve tissue in time sequence and detect a large number of nerve signals that will result spatially and with respect to time. However, metallic electrodes as used in cardiac pacemakers are unsuitable here, since these are recognized as foreign bodies and thus lead to rejection reactions.

Attempts have therefore been made to produce the electrical contact between electronic component and biological tissue with the aid of polymers, such as, for example, silicones or polyurethane. For this purpose, the polymers must however be electrically conductive and additionally biocompatible, i.e. the materials must not give rise to any rejection reaction. In order to be able to contact nerve paths in a specific manner, a structuring of these materials or of the substrates used, for example mini-silicon wafers having dimensions in the region of a few millimeters, is necessary. The size of the structures, such as pyramids or holes, produced in or on the substrate is in a range from 10 µm to about 70 µm.

The most critical element in bioelectronics is the interface between electronics and biological tissue. In order to produce suitable contact, the procedure adopted to date, for example, is first to etch about 25 µm deep pyramidal indentations into a silicon chip. The indentations are then first partly filled with conductive silicone and a second layer of nonconductive silicone is then applied. The polymers are then cross-linked and the structured flexible layer is then removed from the silicon chip. Finally, contact with the silicon protuberances formed on the surface of the flexible layer is produced by individual connecting lines. A similar principle can be used to produce rectangular trenches having tiny dimensions from polyurethane, which trenches can act as microcells for the cultivation of nerve cells.

In order to be able to connect individual neurons specifically to microsystems, supporting structures, such as, for example, trench-like microstructures, are provided on the surface of the substrate. Furthermore, adhesion promoters which facilitate the growth of cells on the surface of the substrate are applied to the surface. In such structures, sown cells grow into network-like structures, and biohybrid systems in the form of microchips covered with cell growth form. Materials which promote cell growth and support the adhesion of the cells are suitable as adhesion promoters at the interface.

In spite of the numerous activities in the area of bioelectronics, this area is still in an experimental stage, so that considerable progress is necessary, particularly in the region of the interface between electronic component and cells, in order to make this area accessible to medical use in practice.

SUMMARY

A method is described for producing biocompatible structures. A chemically amplified photoresist film is provided that contains a first polymer which comprises anchor groups for linking a biocompatible compound and a second polymer which is electrically conductive, wherein the film is applied to a substrate and structured so that a structured resist is obtained. The structured resist is treated with a biocompatible compound so that the biocompatible compound is coordinated to the anchor groups of the first polymer.

A biocompatible microchip having a substrate is also described. The substrate includes microelectronic circuits; and a structured layer which is arranged on the substrate and contains a first polymer which has anchor groups to which a biocompatible compound is coordinated and a second polymer which is electrically conductive.

The invention is explained in more detail below with reference to diagrammatic drawings on the basis of preferred exemplary embodiments of the methods according to the invention.

BRIEF DESCRIPTION OF THE DRAWINGS

The invention is explained in more detail below with reference to the appended drawings, in which, in detail.

DETAILED DESCRIPTION

The following describes a process for producing biocompatible structures that is simple to carry out and permits production of a contact matrix having many contact points. The process employs a technique that may be used in lithographic structuring of semiconductor chips. This technique has been very widely developed and it can be used to produce structures down to the region of less than 100 nm. As already mentioned above, structures having dimensions in the region of about 25 µm are required for bioelectronic applications. Structures having these dimensions therefore can be readily produced using known photoresists and imaging techniques. The first polymer used in the photoresist need only have anchor groups, which permit subsequent linking of biocompatible substances. Subsequent modification of photoresists is already known from the structuring of semiconductors. In this process, the resist structures produced on a substrate are subsequently expanded by linking of expansion reagents in order to be able in this way to produce structures whose dimensions are below the resolution limit of the optical apparatuses used for exposure. Such resists and expansion processes are described, for example, in EP 395 917 B1 and U.S. Pat. No. 5,234,793.

Known electrically conductive polymers may be used as the electrically conductive polymer. These must, if required, be doped or oxidized or reduced in order to convert them into a conductive state. This can also be effected in a separate step after the application of the electrically conductive polymer to the substrate or after the structuring of the resist.

For the production of the biocompatible structures, in principle all chemically amplified photoresists as well as all known structuring processes can be used. All that is necessary is that groups which permit the linking of a biocompatible compound are still present on the structured resist. Both positive and negative chemically amplified photoresists can be used. In the case of the positive chemically amplified resists, the exposed sections of the photoresist are removed by means of a developing solution in the development step, while the unexposed parts remain as lands on the substrate.

This is achieved by virtue of the fact that the exposure liberates a catalyst which changes the polymer of the photoresist in its chemical nature so that a substantial differentiation between exposed and unexposed parts is achieved. This can be achieved, for example, by eliminating groups on the polymer, with the result that the polarity of the polymer increases substantially so that it becomes soluble in aqueous developers.

It is also possible to use negatively structurable resists, in which the exposed parts remain on the substrate as lands while the unexposed parts are removed by means of an aqueous developer. The chemical differentiation between unexposed and exposed sections is generally carried out by a procedure in which the exposure liberates a catalyst which, for example, produces crosslinking of the polymer of the photoresist, with the result that it becomes insoluble in aqueous developers. In the development step, the unexposed parts, which generally have compounds of high polarity, are then removed by means of an aqueous developer. It is also possible to use modified processes which are based on the abovementioned positive and negative chemically amplified photoresist systems.

Such a process is described, for example, in U.S. Pat. No. 4,491,628. There, that layer of a positive photoresist which is applied to a substrate is first exposed, an acid being liberated from a photo acid generator. In the subsequent amplification step, acid-labile groups are eliminated from the polymer in the exposed parts by heating, so that said polymer is now present in a polar form. In contrast to the positive development process described above, development is now not effected with a polar aqueous developer but a nonpolar solvent is used for the development. Consequently, only the unexposed parts in which the polymer has retained its original nonpolar form are detached from the substrate. Since the polar fractions of the resist in which polar groups were produced by the exposure, for example carboxyl groups, are insoluble in nonpolar solvents, they remain as lands on the substrate.

A process as described, for example, in PCT/DE00/04237 can also be used for the production of a structured resist. There, the photoresist contains a photo base as well as a thermo acid. In the exposure of the photoresist, a base is liberated in the exposed parts. If the photoresist is then heated, an acid is liberated from the thermo acid generator. In the exposed parts, the acid is neutralized by the previously liberated base and is therefore no longer available as a catalyst. In the unexposed parts, the acid catalyzes the elimination of acid-labile groups from the polymer. In the unexposed parts, the polymer is therefore converted from its nonpolar form into a polar form. In the subsequent development step, the unexposed parts can therefore be selectively detached from the substrate by means of an aqueous alkaline developer, whereas the exposed parts remain as lands on the substrate.

In all of these processes, it is essential that groups for binding the biocompatible compound are still available after the structuring of the photoresist.

However, a process as described in EP 0 395 917 B1 is preferably used for structuring the photoresist. In this case, the photoresist used is a positive photoresist to which, after exposure, amplification and development, the biocompatible compound is linked in a further step.

In this embodiment, the process comprises steps of applying a photoresist film to a substrate, the photoresist film containing a first and second polymer and a photo acid generator. The first polymer comprises acid-labile groups which, after their elimination, liberate a polar group with the result that the solubility of the first polymer in aqueous alkaline developers is increased, and which furthermore has anchor groups for linking a biocompatible compound, it also being possible for the anchor groups to be present in protected form. The second polymer is electrically conductive, it being possible to arrange the first and second polymer as a mixture or as successively arranged layers on the substrate. Other steps includes section-by-section exposure to the photoresist film; heating of the exposed photoresist film, the acid-labile groups being eliminated from the polymer in the exposed sections; and developing the exposed and heated photoresist film with an aqueous alkaline developer solution, the exposed sections of the photoresist film being detached from the substrate and a structured resist being obtained. Optionally, the layer of the electrically conductive second polymer may be etched, or the anchor groups of the first polymer may be liberated. Steps are then performed for application of a solution of a biocompatible compound, the biocompatible compound being coordinated to the anchor groups of the first polymer, and removal of excess solution of the biocompatible compound.

This embodiment of the process according to the invention can be carried out by two methods, the first and the second polymer being contained either in a common layer or in two layers separated from one another. In the first-mentioned method, a solution which contains the first polymer, the second polymer and the photo acid generator in a suitable solvent is applied to the substrate. By evaporating the solvent, a photostructurable film which is structured by conventional lithographic methods is obtained. The biocompatible compound which is coordinated to the anchor groups of the first polymer is then applied as described above.

According to a second method, a first and second polymer are applied in separate layers to the substrate. First, a first layer of the second, electrically conductive polymer is produced on the substrate. The second layer, which contains the first polymer and the photo acid generator, is then produced thereon. The second layer of the first polymer is then exposed and developed and thus structured. This structure is then transferred to the first layer which contains the electrically conductive second polymer, for which purpose, for example, a suitable plasma is used. Once again, the biocompatible compound which is coordinated to the anchor groups of the first polymer is then applied.

According to a further preferred embodiment of the process, a layer which comprises the first polymer and the photo acid generator is produced on the substrate. The layer is then exposed section-by-section and developed and a structured layer is thus obtained. A layer of the second polymer is then applied to the structured layer.

In this embodiment, the process is preferably carried out in a manner such that the second polymer can penetrate into the first polymer. For this purpose, the second polymer is applied as a solution in a suitable solvent to the structured layer. For this purpose, the solvent must be such that, on the one hand, it does not dissolve the structure of the structured layer but, on the other hand, partially dissolves or swells the first polymer to such an extent that the second polymer can penetrate sufficiently deeply.

Preferably, the second polymer is coordinated to the first polymer, for example via the anchor groups provided in the first polymer.

First polymers used for the photoresist may be those polymers which, after development, still have groups to which the biocompatible compound can coordinate. The first polymers must have adequate film formation properties in order to be able to produce a uniform film of the photoresist on the substrate. It is possible to use all polymers which have, in the polymer chain or as side groups, acid-labile groups which possess low alkali solubility and produce polar groups, for example acidic groups, on the polymer by catalytic action of acid and optionally simultaneous heat treatment (contrasting). Examples of suitable acid-labile groups are: tert-alkyl ester, tert-butoxycarbonyloxy, tetrahydrofuranyloxy, tetrahydropyranyloxy, tert-butyl ether, lactone or acetal groups. tert-Butyl ester groups are particularly preferred.

The film-forming polymer can therefore be obtained by polymerization or copolymerization of corresponding monomers. Suitable monomers are, for example, acrylates, methacrylates, maleic monoesters and diesters, itaconic monoesters and diesters, norbornenecarboxylic esters or norbornenecarboxylic monoesters and diesters. Appropriate repeating units of the polymer are shown below. Y is a radical which can be eliminated by acid, as contained, for example, in one of the abovementioned groups and after whose elimination the polar group, for example, a carboxyl or hydroxyl group, is liberated, and R1 is a non-acid-labile radical, for example an alkyl group having 1 to 10 carbon atoms. Furthermore, n is an integer between 1 and 10.

The elimination of the acid-labile radical from the acid-labile group with liberation of the polar group is shown below by way of example for two preferred repeating units. In the first example, the repeating unit comprises a tert-butyl ester group, from which a carboxyl group is liberated under the action of acid.

-continued

In the second example, the acid-labile group comprises a tert-butoxycarbonyloxy radical which is bonded to a phenolic hydroxyl group. Under the action of acid, an acidic hydroxyl group is therefore liberated as a polar group.

These monomers can be copolymerized with further monomers. A suitable monomer is, for example, styrene. In addition to said monomers, other monomers customary for the preparation of polymers contained in photoresists can also be used. For example, cycloaliphatic groups can be introduced by copolymerization of norbornene and norbornene derivatives. Silicon-containing groups can be introduced by copolymerization of trialkylallylsilanes. The exact composition of the polymer depends on the properties which are required for the further processing. If the photoresist is used, for example, also for etching the substrate, said photoresist must have sufficient etching resistance. This is achieved by introducing silicon-containing groups, aromatic groups or alicyclic groups into the polymer.

Photo acid generators used may be the photo acid generators customary for photoresists. Onium compounds as described, for example, in EP 0 955 562 A1, are preferably used.

For example, methoxypropyl acetate, cyclopentanone, cyclohexanone, g-butyrolactone, ethyl lactate, diethylene glycol dimethyl ether or a mixture of at least two of these compounds can be used as a solvent of the resist. In general, however, all conventional solvents or mixtures thereof which are capable of taking up the resist components in a clear, homogeneous solution having a long shelf-life and which ensure a good layer quality on coating of the substrate can be used.

The photoresist is applied to the substrate by the conventional methods, for example by spin-coating, spraying on, immersion or brush methods. The solvent is then removed by conventional methods. In general, the substrate with the resist film is heated for this purpose.

The second polymer, which is electrically conductive, can be applied as a mixture with the first polymer or as a separate layer. Many electrically conductive polymers must be deposited so that high crystalline order is achieved in the deposited solid. In this case, the deposition of the electrically conductive second polymer is effected in a separate layer, the layer of the first polymer being arranged on the layer of the second polymer. The second polymer may already be conductive during its deposition or can be converted into its conductive state only subsequently by oxidation or reduction.

Exposure of the resist film is then effected, for which purpose the conventional methods may likewise be used. The exposure can be effected, for example, by means of a photo mask or by direct exposure using focused electrons or ions. The exposure radiation preferably has a wavelength in the range from 10 to 400 nm. Since a particularly high resolution is not required for the biocompatible structures, light having a wavelength of 365 nm, 248 nm or 193 nm is usually used, as is also employed in the production of microchips. In the exposed parts, an acid is liberated from the photo acid generator, wherein a latent image of the desired structure is formed. The exposure of the resist film is followed by a contrasting step in which the latent image is amplified and impressed into the polymer of the photoresist so that the photoresist now has a chemical profile. For this purpose, the substrate with the exposed resist film is heated, in general to temperatures of 80 to 200° C. During the heating, the acid-labile groups on the polymer are eliminated under the catalytic influence of the acid and polar groups are liberated. The polymer now has a high polarity and hence solubility in polar solvents. The exposed parts can therefore be removed by means of an aqueous alkaline developer solution. For example, a 2.38% strength solution of tetramethylammonium hydroxide in water can be used as the developer solution. After the development, a structured resist which has the structures to which the cells are to be bound subsequently is obtained. Depending on which second polymer is used, it may be necessary to transfer the structure produced with the first polymer into the layer of the second polymer. For this purpose, for example, it is possible to carry out an etching step in which the second polymer is removed in the regions where it is not covered by the first polymer.

In order to be able to introduce the biocompatible compound into the structured photoresist, the polymer must have corresponding anchor groups for linking a biocompatible compound. For this purpose, it is possible to adopt a procedure in which the structured photoresist which still comprises acid-labile groups is exposed to a floodlight. An acid is now likewise liberated in the previously unexposed parts. On heating, the acid-labile groups are now likewise eliminated and polar groups, for example carboxyl groups or acidic alcoholic groups, such as, for example, acidic phenolic groups, are liberated. These can then be used as anchor groups for the coordination of the biocompatible compound. It is also possible additionally to provide a thermo acid generator in the photoresist. The structured photoresist can then be heated, the acid being liberated and the acid-labile groups also being eliminated.

After the liberation of the anchor groups by the elimination of the acid-labile groups, a solution of the biocompatible compound is applied to the structured resist. The solvent is chosen so that the structured resist is not detached from the substrate and at the same time the biocompatible compound is taken up by the solvent in the form of a solution or of an emulsion. For example, buffered aqueous solutions are suitable. The biocompatible compound, which has a suitable coordination group, now coordinates to the anchor groups of the polymer. This need not necessarily take place with the formation of a covalent bond. The coordination of the biocompatible compound to the anchor group of the polymer can also take place with salt formation if, for example, the anchor groups on the polymer are formed by carboxyl groups and the coordinate group on the biocompatible compound is formed by an amino group. Coordination by dipole-dipole interaction is also possible, provided that sufficiently strong immobilization of the biocompatible compound in the photoresist is effected. Such coordination of the biocompatible compound to the anchor group of the polymer by noncovalent bonds has the advantage that the bonding is reversible. If, for example, growth factors are added as the biocompatible compound to the structured resist, they can be taken up by the cells and hence the cell growth can be influenced.

In some cases, it may be preferable if the biocompatible compound is bonded to the polymer of the photoresist by a covalent bond. The formation of a covalent bond can be effected in a downstream step by heating the photoresist and, for example, forming an amide bond from an ammonium carboxylate with elimination of water.

The coordination of the biocompatible compound with formation of a covalent bond can also be effected by a reaction with suitable groups of the polymer. For this purpose, the anchor groups for binding the biocompatible compound in the polymer are formed as reactive anchor groups. A reactive anchor group is understood as meaning an anchor group in the polymer to which the biocompatible compound is coordinated with formation of a covalent bond. The reactive anchor group has sufficient reactivity to permit the formation of a chemical bond to the biocompatible compound within sufficient short reaction times. Suitable groups are, for example, carboxylic anhydrides, epoxides, isocyanates, glycidyl ethers, amines, alkyl halides, thiols and acyl halides.

Particularly preferably, the polymer comprises carboxylic anhydride groups as reactive anchor groups. These can be introduced into the polymer by, for example, copolymerizing maleic anhydride, itaconic anhydride, methacrylic anhydride, cyclohexenedicarboxylic anhydride or norbornenecarboxylic anhydride during the preparation of the polymer. Exemplary repeating units of the polymer, which have a dicarboxylic anhydride function, are shown below:

$R^2$ is preferably hydrogen or any other radical, in particular an alkyl radical having 1 to 10 carbon atoms. The radicals $R^2$, independently of one another, may have the same meaning.

As already mentioned, the biocompatible compound must have a suitable coordination group for coordination to an anchor group of the polymer. Particularly preferably, the biocompatible compound comprises an amino group and/or a hydroxyl group, via which the biocompatible compound is coordinated to the anchor group of the polymer. The coordination can be effected via an individual group or via a plurality of groups. The coordination is effected, for example, by the reaction of the amino group with a carboxylic anhydride with formation of an amide bond or of an imido group. If a hydroxyl group of the biocompatible compound is used for the coordination, an ester group is correspondingly formed. Such bonds can be enzymatically cleaved by cells, so that the biocompatible compound can be eliminated again from the resist as a cell during the growth of the cell.

All compounds which facilitate growth of cells on the structures produced from the photoresist can in principle be used as the biocompatible compound. Some of these compounds may be high molecular weight biological compounds. In a preferred embodiment, the biocompatible compound comprises a spacer which carries the amino group or the hydroxyl group for the coordination of the biocompatible compound to the anchor group of the polymer. This facilitates binding of high molecular weight compounds to the polymer, since the steric hindrance is reduced. In addition, the action of the biocompatible compound improves if it is separated from the surface of the structured resist by means of a spacer. Techniques for immobilizing high molecular weight compounds on the surfaces are known, for example, from the immobilization of antigens on high molecular weight proteins. Corresponding techniques can also be used for the coordination of the biocompatible compound to the anchor groups of the polymer.

The biocompatible compound used is preferably an amino acid or a peptide. These compounds already contain groups, for example amino groups, which can be used for the coordination of the biocompatible compound to the polymer of the resist. Peptides used may be, for example, growth factors. The amino acid or the peptide can in turn also be used as a coordination site to which the corresponding growth-promoting factors are reversibly bound. During the growth of the cells, these factors are then removed from the surface of the structured resist and taken up by the cells.

According to a further advantageous embodiment, the biocompatible compound is an oligomeric or polymeric urethane. Urethanes can be enzymatically cleaved by cells. Such compounds therefore promote the growth of cells.

In order to achieve better transmission of electrical signals between cells and electronic component, the resist structure comprises an electrically conductive polymer as the second polymer. It is possible to use all electrically conductive organic materials per se. For example, the electrically conductive polymer can be selected from the group consisting of electrically conductive polyaniline, electrically conductive polythiophene, electrically conductive polypyrrole and electrically conductive polyvinylphenylene.

In principle, all materials which are compatible with the growth of cells can be used as the substrate. Thus, for example, polymeric materials or semiconductors, such as, for example, silicon, can be used. Since the structured resist is to be used for information transmission between microelectronics and cells, for example by transmission of electrical signals, the substrate is preferably a microchip. This may comprise corresponding microelectronic circuits.

The invention also relates to a biocompatible microchip comprising a substrate which comprises microelectronic circuits and a structured layer which is arranged on the substrate and contains a first polymer which has anchor groups to which a biocompatible compound is coordinated and a second polymer which is electrically conductive.

According to a preferred embodiment, the biocompatible microchip has a structure in which the first polymer and the second polymer is [sic] arranged in separate layers. Preferably, the first polymer is contained in a layer which is arranged on the layer of the second polymer.

Figure 1A:
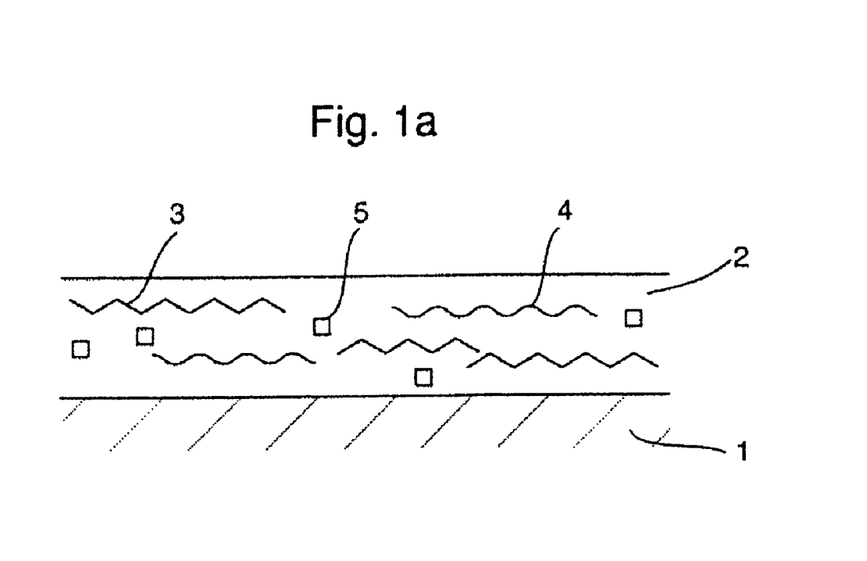
FIGS. 1A-1C illustrate a sequence of process steps according to a first preferred embodiment of the process according to the invention.
Figure 1B:
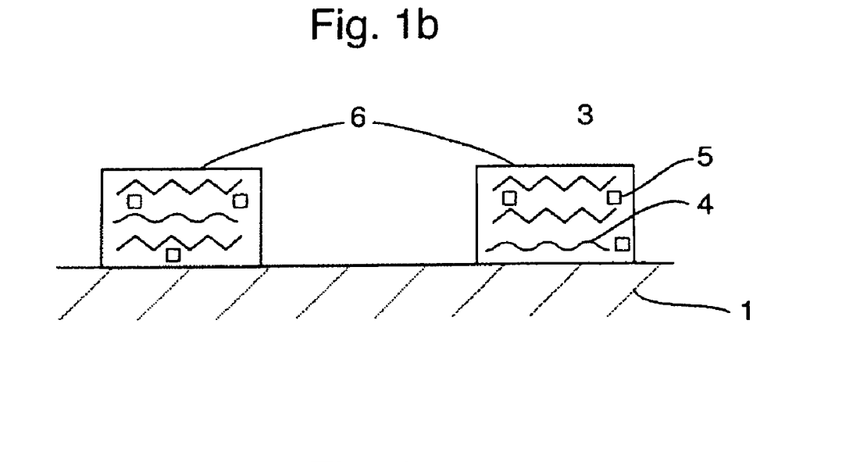
Figure 1C:
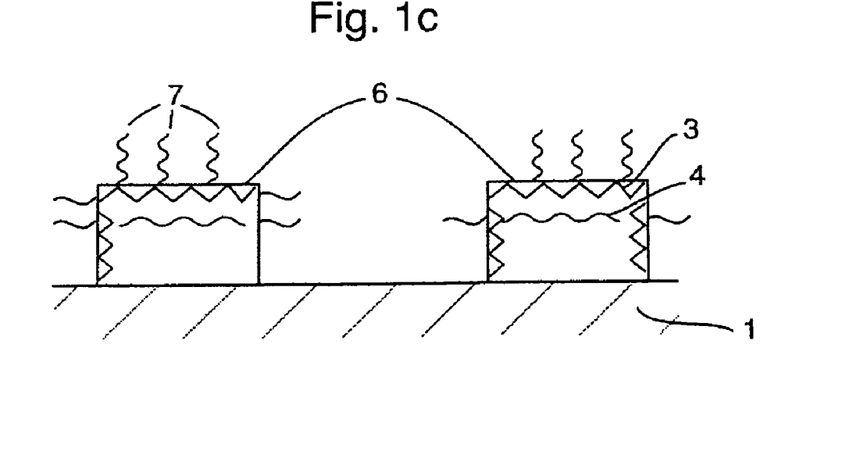
Figure 2A:
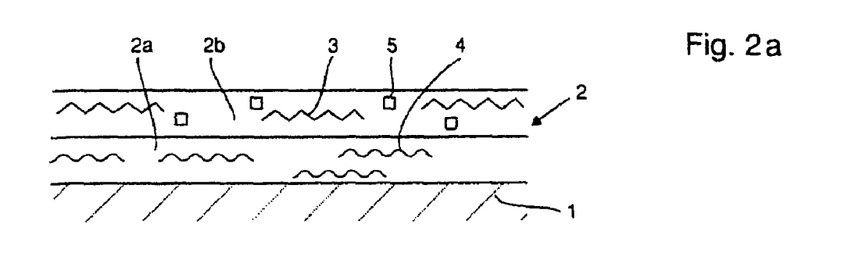
FIGS. 2A-2D illustrate a sequence of process steps according to a second preferred embodiment of the process according to the invention.
Figure 2B:
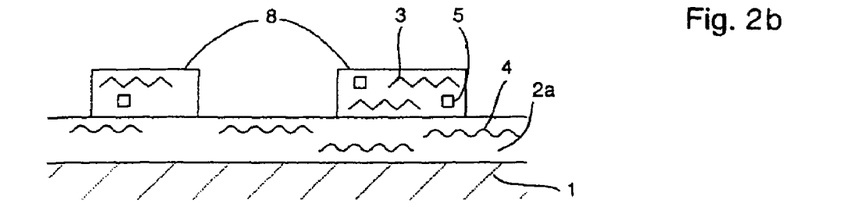
Figure 2C:
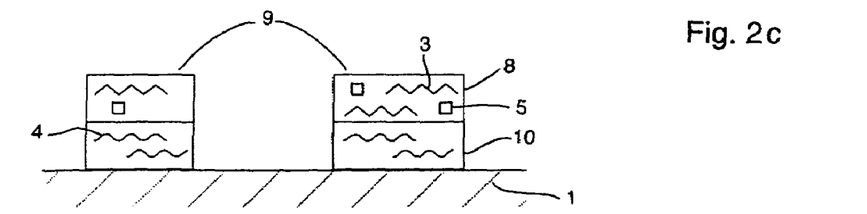
Figure 2D:
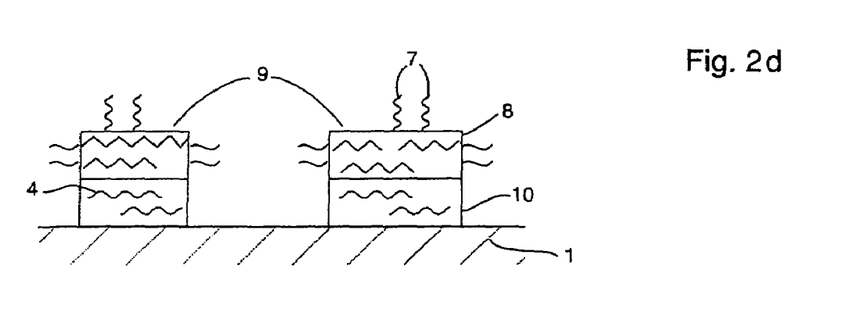

FIG. 1 shows the process steps which are implemented if the first and second polymer are contained in a common layer. For this purpose, as shown in FIG. 1a, a photoresist film 2 is applied to a substrate 1, for example a microchip, in which electronic circuits are already integrated. The first polymer 3, the second polymer 4 and the photo acid generator 5 are contained in the photoresist film 2. The photoresist film 2 is then exposed section-by-section and developed so that the structured resist shown in FIG. 1b is obtained. This comprises raised sections 6 which are arranged on the substrate 1 and are formed from the material of the photoresist film 2 and therefore contain the first polymer 3, the second polymer 4 and the photo acid generator 5. A solution of the biocompatible compound, which is coordinated to the first polymer 3, is then applied. This can be effected immediately after the structuring of the photoresist film, provided that the first polymer 3 has corresponding anchor groups. Otherwise, exposure to a floodlight is first effected so that acid is liberated from the photo acid generator 5 still present. It is then heated for cleavage of the acid-labile groups, polar groups acting as anchor groups being liberated. The coordination of the biocompatible compound 7 to the anchor groups of the first polymer 3 is shown schematically in FIG. 1c. The biocompatible compound 7, which is fixed by coordination to the first polymer 3, has accumulated at the outer surfaces of the raised sections 6. Cells can then be sown on this structure.

In that embodiment of the process according to the invention which is shown in FIG. 2, the first and the second polymers are arranged in separate layers. For this purpose, first, as shown in FIG. 2a, a two-layer photoresist film 2 is produced, which film comprises a first layer 2a of the second, electrically conductive polymer 4, which is arranged on the substrate 1, and a second layer 2b which is arranged on this first layer 2a and contains the first polymer 3 and the photo acid generator 5. The photoresist film 2 is then exposed section-by-section and developed so that the second layer 2b is structured. This state is shown in FIG. 2b. Raised sections 8 which contain the first polymer 3 and the photo acid generator 5 have formed on the layer 2a. The structure formed by the raised sections 8 is now transferred to the first layer 2a of the electrically conductive second polymer 4. As shown in FIG. 2c, raised sections 9 which, in their upper section, are formed by the sections 8 of the first polymer 3 and, in their lower section, by the section 10 of the second polymer 4 are now arranged on the substrate 1. The anchor groups of the first polymer 3 can now optionally be liberated and then a solution of the biocompatible compound 7 which coordinates to the molecules of the first polymer 3 can be applied. As shown in FIG. 2d, biocompatible molecules 7 are coordinated to the outer surfaces of the section 8 of the raised structures 9. This structure can then be populated again by cells.

Figure 3A:
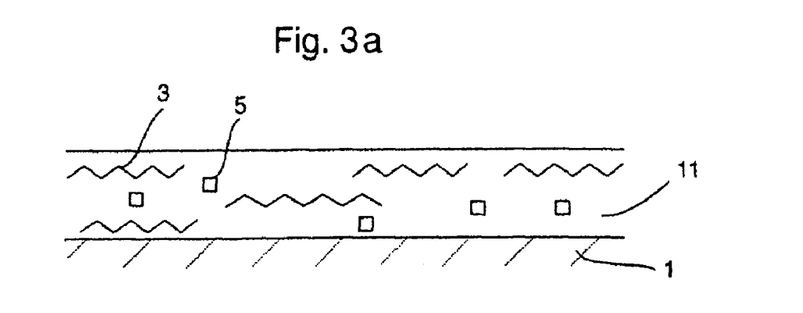
FIGS. 3A-3D illustrate a sequence of process steps according to a third preferred embodiment of the process according to the invention.
Figure 3B:
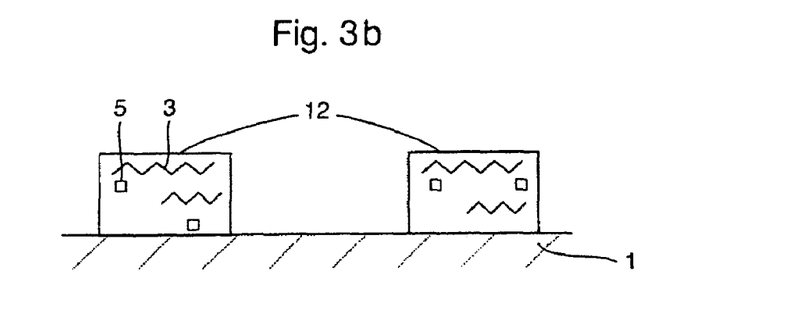
Figure 3C:
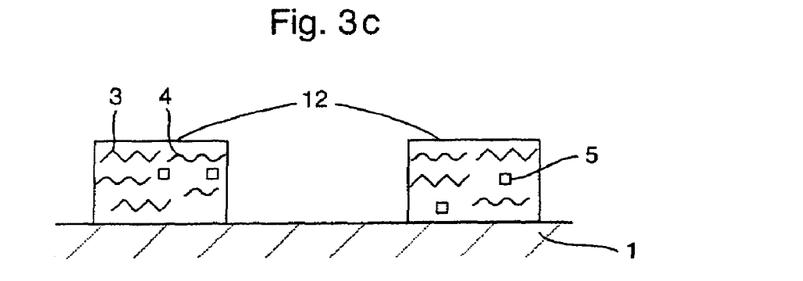
Figure 3D:
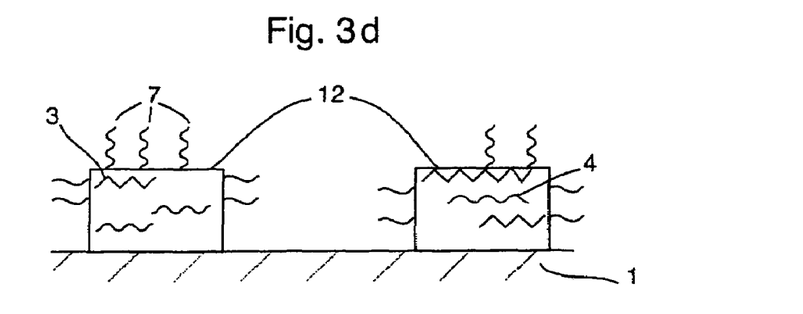

In the process sequence shown in FIG. 3, a resist structure is first produced from the first polymer 3, and the electrically conductive second polymer 4 is subsequently introduced. For this purpose, a layer 11 which contains the first polymer 3 and the photo acid generator 5 is first produced on the substrate 1. This arrangement shown in FIG. 3a is now exposed section-by-section and develops so that the arrangement shown in FIG. 3b is obtained. Raised regions 12 which contain the first polymer 3 and the photo acid generator 5 are arranged on the substrate 1. A solution of the second polymer 4 in a suitable solvent is now applied. The solvent swells or partially dissolves the raised sections 12 so that the second polymer 4 can penetrate. Since the raised sections 12 have relatively large dimensions and also the preservation of the structure of these sections 12 on introduction of the second polymer 4 is not critical, slight detachment at the raised sections 12 is acceptable. The biocompatible compound is then once again added as a solution, optionally after liberation of the anchor groups on the first polymer 3, so that, as shown in FIG. 3d, the biocompatible compound 7 can be coordinated to the outer surfaces of the raised regions 12.

The invention provides a process which is based on lithographic processes which have already been used industrially for the production of microchips. Considerable knowledge is therefore already available for carrying out the process. Structures with dimensions required for bioelectronic applications can be readily produced by these processes. The structured resist remains on the substrate and, after appropriate conditioning by a biocompatible compound, is covered with cell growth. The electrically conductive polymer contained in the structured resist layer produces an improved contact with the cells, which permits better signal transmission.

The foregoing disclosure of embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

What is claimed is:

1. A method for producing biocompatible microchips, the method comprising:
   fabricating a microchip comprising microelectronic circuits;
   depositing a chemically amplified photoresist film over the fabricated microchip, wherein the chemically amplified photoresist film comprises:
      a first polymer which comprises acid-labile groups which, after their elimination, liberate a polar group with the result that the solubility of the first polymer in aqueous alkaline developers is increased, and which furthermore has anchor groups for linking a biocompatible compound, it also being possible for the anchor groups to be present in protected form;

a photo acid generator; and a second polymer which is electrically conductive, it being possible to arrange the first and second polymers as a mixture or as successively arranged layers on the microchip;

exposing the chemically amplified photoresist film section-by-section;

heating the exposed chemically amplified photoresist film to eliminate the acid-labile groups from the first polymer in the exposed sections;

developing the heated chemically amplified photoresist film by means of an aqueous alkaline developer solution to form a structured resist, wherein the developing detaches the exposed sections of the photoresist film from the microchip;

applying a solution of a biocompatible compound over the structured resist, the biocompatible compound being coordinated to the anchor groups of the first polymer; and removing excess solution of the biocompatible compound to form a biocompatible structured resist, wherein the biocompatible compound influences growth of cells on the biocompatible structured resist, and wherein the biocompatible structured resist enables information transfer between the cells and the microchip via electrical signals.

2. The method of claim 1, wherein a layer which comprises the first polymer and the photo acid generator is produced on the microchip, the layer being structured so that a structured layer is obtained, and a layer of the second polymer is applied to the structured layer.

3. The method of claim 2, wherein the second polymer is being applied as a solution to the structured layer.

4. The method of claim 2, wherein the second polymer is coordinated to the first polymer.

5. The method of claim 4, wherein the anchor groups for linking the biocompatible compound are in the form of reactive anchor groups to which the biocompatible compound is coordinated with formation of a covalent bond.

6. The method of claim 5, wherein the reactive anchor group is selected from a group consisting of carboxylic anhydride, epoxide, isocyanate, glycidyl ether, amine, alkyl halide, thiol and acyl halide.

7. The method of claim 5, wherein the biocompatible compound has an amino group and/or a hydroxyl group, via which the biocompatible compound is coordinated to the anchor group of the first polymer.

8. The method of claim 7, wherein the biocompatible compound comprises a spacer which carries the amino group or the hydroxyl group for the coordination of the biocompatible compound to the anchor group of the first polymer.

9. The method of claim 1, wherein the biocompatible compound comprises an amino acid or a peptide.

10. The method of claim 1, wherein the biocompatible compound is an oligomeric or polymeric urethane.

11. The method of claim 1, wherein the electrically conductive polymer is selected from the group consisting of electrically conductive polyaniline, electrically conductive polythiophene, electrically conductive polypyrrole and electrically conductive polyvinylphenylene.

12. A method for producing biocompatible microchips, the method comprising:

fabricating a microchip comprising microelectronic circuits;

depositing a chemically amplified photoresist layer over the fabricated microchip, wherein the chemically amplified photoresist layer comprises an electrically conductive polymer;

patterning the chemically amplified photoresist layer;

depositing a biocompatible compound over the patterned chemically amplified photoresist layer; and forming a chemical bond at an interface between the biocompatible compound and the patterned chemically amplified photoresist layer, wherein the biocompatible compound is in electrical contact with the microchip via the patterned chemically amplified photoresist layer.

13. The method of claim 12, wherein the electrical contact enables transmission of information between the microchip and cells grown over the biocompatible microchips.

14. The method of claim 12, wherein the biocompatible compound bonded to the patterned chemically amplified photoresist layer influences the growth of cells over the biocompatible microchips.

15. The method of claim 12, wherein the chemical bond is formed by linking the biocompatible compound to anchor groups in the photoresist, wherein the biocompatible compound comprises groups with suitable coordination to link with the anchor groups in the photoresist.

16. The method of claim 12, wherein forming a chemical bond comprises forming a non-covalent bond.

17. The method of claim 12, wherein the photoresist further comprises a polymer comprising anchor groups for linking the biocompatible compound, and acid-labile groups which, after their elimination, result in increased solubility of the polymer in aqueous alkaline developers.

* * * * *